United States Patent [19]

Tiep

[11] 4,074,710
[45] Feb. 21, 1978

[54] INTRATHORACIC PRESSURE BIOFEEDBACK METHOD

[75] Inventor: Brian L. Tiep, Monrovia, Calif.

[73] Assignee: City of Hope National Medical Center, Duarte, Calif.

[21] Appl. No.: 690,851

[22] Filed: May 28, 1976

[51] Int. Cl.² ............................................. A61B 5/02
[52] U.S. Cl. ........................ 128/2.05 P; 128/2.05 R; 35/22 R
[58] Field of Search ...................... 128/2.05 P, 2.05 T, 128/2.05 R, 2.05 S, 2.06 R, 2.06 F, 2.06 A; 35/22 R, 17

[56] References Cited

U.S. PATENT DOCUMENTS

| | | | |
|---|---|---|---|
| 2,918,054 | 12/1959 | Goolkasian | 128/2.05 T |
| 3,426,150 | 2/1969 | Tygart | 128/2.06 R X |
| 3,541,590 | 11/1970 | Settler et al. | 128/2.05 P |
| 3,599,628 | 8/1971 | Abbenante | 128/2.06 F X |
| 3,650,264 | 3/1972 | Janssen | 128/2.06 A |
| 3,742,938 | 7/1973 | Stern | 128/2.05 T |
| 3,830,227 | 8/1974 | Green | 128/2.06 R |
| 3,895,316 | 7/1975 | Fein | 128/2.05 P |
| 3,908,636 | 9/1975 | Page | 128/2.05 T |

OTHER PUBLICATIONS

Fried, "Biofeedback: Teaching Your Body to Heal Itself", Reader's Digest, May 1974, pp. 110–113.
Waite, "Alpha Brain Waves & Biofeedback Training", Popular Electronics, Dec. 1972, pp. 33–38.

*Primary Examiner*—Ronald L. Frinks
*Assistant Examiner*—Lee S. Cohen
*Attorney, Agent, or Firm*—Edward D. O'Brian

[57] ABSTRACT

The pulse of a patient suffering from an obstructive lung ailment or problem such as emphysema, bronchiectasis, chronic bronchitis, asthma or the like may be monitored so as to obtain a signal varying in accordance with the peak values of successive pulse beats. The signal so obtained is used to provide an output to the patient which is capable of being sensed by the patient and which corresponds to the differences in the peak values of successive pulse beats. This output is used by the person in learning to control the operation of his or her heart in order to reduce the work of breathing and to avoid potential eventual heart failure when the individual encounters breathing problems.

3 Claims, 1 Drawing Figure

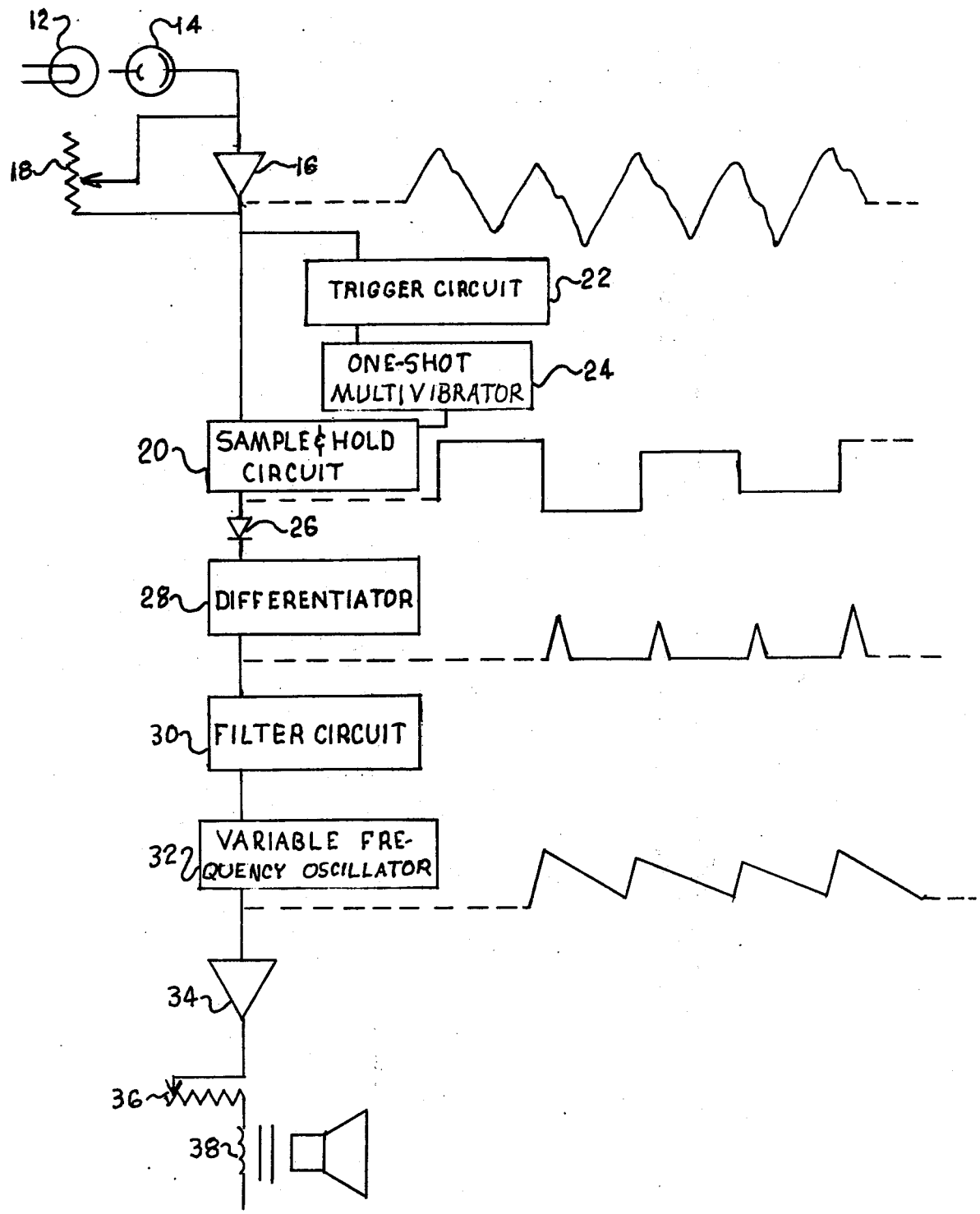

INTRATHORACIC PRESSURE BIOFEEDBACK METHOD

CROSS-REFERENCE TO RELATED APPLICATIONS

The subject matter of this application is to a degree related to the subject matter disclosed and claimed in the co-pending application by the inventor named herein, Brian L. Tiep, entitled "METHOD AND APPARATUS FOR TREATING BRONCHIAL ASTHMA", Ser. No. 690,850, filed May 28, 1976.

BACKGROUND OF THE INVENTION

The invention set forth in this specification pertains to a new and improved method and apparatus for use by a patient suffering from obstructive lung ailments such as emphysema, bronchiectasis, chronic bronchitis, asthma or the like in learning to control breathing so as to minimize the work of breathing and/or to minimize or eliminate the strain on the patient's heart.

An understanding of the present invention is not considered to require a detailed understanding of various types of obstructive lung ailments such as those noted in the preceding paragraph. It is considered, however, that an understanding of the invention requires a generalized understanding of the relationship between the breathing of a patient suffering from such an ailment and the operation of the patient's heart. It is, of course, obvious that any individual suffering from an obstructive lung problem has difficulty in breathing, the amount of such difficulty varying in accordance with the nature and extent of the individual's ailment.

As a consequence of this difficulty in breathing an individual with an obstructive lung problem will normally tend to realize when he or she is in need of air so as to replenish the oxygen in the blood. As an individual becomes aware of an increasing need to speed up or facilitate his or her breathing process the individual will normally react so as to cause his or her heart to pump harder than normal in an effort to circulate his or her blood to the lungs so that the oxygen content of the blood can be replenished. As this occurs there is a resulting increase in the pressure within the chest of the individual. The pressure within this area of the body is normally referred to as the intrathoracic pressure.

As the intrathoracic pressure of an individual suffering from an obstructive lung ailment increases as a consequence of increased heart activity what may be referred to or regarded as a "self-defeating" type action will normally tend to come about. The increased pressure will tend to close off and/or constrict various passages and parts of the breathing system. Further, as there is increasing intrathoracic pressure such pressure in many cases tends to promote the accumulation of fluid in the alveolar sacks within the lungs. Both of these "consequences" tend to impede the gas transfer which is necessary for the oxygen content of the blood to be replenished. As a result of these factors as an individual tends to react so as to cause his or her heart to work harder than normal in an effort to maintain the oxygen content of the blood the action of the heart itself in circulating the blood will tend to increase the intrathoracic pressure in such a way as to increasingly impede breathing.

As the heart activity becomes more and more pronounced in response to an individual's need to replenish the oxygen content of the blood there is significant danger of heart decompensation or failure. Although the pumping action of the heart can be controlled through the use of appropriate known medicants so as to prevent heart failure as the heart increases its activity in an effort to maintain the normal oxygen content of the blood the use of such drugs has limitations. The problem of the heart pumping action increasing as an individual is trying to achieve adequate breathing may occur when the individual is unable for one reason or another to utilize an appropriate drug.

As a result of this consideration, it is believed that there is a distinct need for a procedure whereby an individual suffering from an obstructive lung ailment or problem can learn or can be taught to control his or her heart action so as to minimize the work of breathing and so as to minimize the possibility of heart failure when such an individual encounters breathing problems. It is also considered that there is a need for an apparatus for use by an individual in learning to control heart action during breathing difficulties so that the individual can, through the use of the apparatus, learn to breathe in such a manner as to promote a desired breathing action.

SUMMARY OF THE INVENTION

A broad objective of the present invention is to fulfill the needs indicated in the preceding discussion. In its more detailed aspects the invention is intended to provide a new and improved method of a very simple, effective character for use by an individual in learning to control heart action so as to reduce the work of breathing and to avoid eventual heart failure when the individual encounters breathing problems. The invention set forth herein is also intended to provide a new and improved apparatus of a relatively inexpensive, effective character is providing a biofeedback type of signal which can be sensed by an individual so that the individual can learn to control heart action in accordance with the output or output signal from the apparatus. A further objective of the invention is to provide an apparatus as described which may be easily and conveniently used.

The process in accordance with this invention for treating a patient suffering from an obstructive lung disorder utilizes biofeedback in order to teach the patient how to control his or her breathing and comprises the steps of monitoring the pulse of the patient so as to obtain a signal varying in accordance with the peak values of the pulse and providing to the patient an output corresponding to this signal which is capable of being sensed by the patient, this output indicating the differences in the peak values of successive pulse beats. An apparatus in accordance with this invention comprises monitoring means for monitoring the pulse of the patient so as to obtain a signal corresponding to the amplitude of the pulse beats of the individual, signal modification means for providing a signal corresponding to only the differences in the amplitudes of successive monitored pulse beats and output means providing an output from the signal provided by the signal modification means corresponding to the differences of the peak values of successive pulse beats which is capable of being sensed by the patient.

BRIEF DESCRIPTION OF THE DRAWING

It is considered that the invention is best more fully delineated by referring to the accompanying drawing in which:

The FIGURE is a diagrammatic figure showing the circuit of a presently preferred apparatus in accordance with the invention, this view being accompanied by curves adjacent to certain circuit components indicating the nature of the outputs of these circuit components.

The invention set forth herein is set forth and defined in the appended claims forming a part of this disclosure. The principles or features set forth in these claims are utilized in connection with the illustrated apparatus. It is considered that they can be easily utilized in connection with other somewhat differently constructed apparatuses through the use or exercise of routine electronic skill in the biofeedback field.

DETAILED DESCRIPTION

The invention set forth in this specification is a type of biofeedback method. In accordance with biofeedback procedures a body condition capable of being controlled by a person is monitored so as to provide a signal or output indicating this condition. This signal or output is then sensed by the person so that the person can control the body performance in accordance with the output signal or indication. Biofeedback methods or procedures have been utilized for a variety of purposes such as, for example, in teaching individuals to control their pulse rates, in teaching individuals to develop certain manners of operating their minds, and so on.

Although biofeedback methods have been known for some time it has not been recognized that these methods are capable of uses in treating many specific types of ailments. In those cases where biofeedback methods have been successful normally they have been utilized in connection with a body condition capable of being directly sensed or determined so as to provide a signal or output directly corresponding to the body condition. Many ailments are of such a character that it is impossible to directly monitor a body condition indicating such an ailment. This is the case in connection with various types of obstructive lung ailments or problems such as emphysema, bronchiectasis, chronic bronchitis, asthma or the like.

Although it has been recognized that the pressure within the chest cavity or the intrathoracic pressure of an individual or patient suffering from an obstructive lung problem is an indication of the difficulty such an individual has in breathing, in the past there has been no convenient way of monitoring the intrathoracic pressure so as to determine the relative difficulty the individual has in breathing at a particular time interval. This intrathoracic pressure has, of course, been capable of being measured by utilizing a balloon type structure inserted into the appropriate breathing passages so as to transmit pressure to a transducer during breathing. It has also been measured by inserting a needle into the pleura.

It is considered obvious that neither of these methods of measuring the intrathoracic pressure is of such a character as to be capable of being utilized in monitoring the breathing of a patient so as to provide a continuous signal indicating that the patient may be breathing in a manner having undesired consequences for the patient. As indicated in the preceding discussion when an individual suffering from an obstructive lung ailment encounters difficulty in breathing normally the individual's body will react so as to tend to increase the heart pumping action in an effort to circulate increasing quantities of blood to the lungs.

As this occurs breathing by the individual will become more and more difficult and this difficulty will tend to increase in accordance with the increase in intrathoracic pressure. Concurrently as the heart works harder in an effort to circulate increasing quantities of blood to the lungs there will be an increasing possibility of heart decompensation or failure. As this occurs the pressure of the blood in the veins leading to the heart tends to increase.

Such blood pressure increase is also manifested throughout the body, including within the lungs. In accordance with this invention this increase in blood pressure is monitored so as to provide to an individual a signal which directly correlates with the blood pressure and which therefore correlates with the intrathoracic pressure to an accurate enough extent so that the individual in obtaining an output signal can learn to control the action of his or her heart to a sufficient extent to minimize or reduce the work of breathing and to avoid the danger of heart damage or failure as he or she is experiencing difficulty in breathing.

Although the pulse may be monitored in many different ways in accordance with this invention it is preferred to utilize a monitoring means consisting of a light source 12 capable of emitting light of a constant intensity separated by a photocell 14 a sufficient distance so that the tip of a finger of an individual may be inserted between the light source 12 and the photocell 14. Preferably any convenient strap arrangement or the like is used to hold such a finger immobile so that the photocell 14 will provide an output signal to an amplifier 16 which will reasonably correspond to the pulse of an individual as manifested by the amount of blood in the tip of the finger at any particular interval.

A conventional variable resistor 18 is provided around the amplifier 16 for the purpose of varying the output of the amplifier 16. This amplifier 16 is used to provide a signal approximating variations in an individual pulse which may have a shape or configuration roughly as indicated by the curve adjacent to the amplifier 16. This signal from the amplifier 16 is supplied to a conventional sample and hold or peak sampler type circuit 20 and also is supplied with a conventional trigger circuit 22. The output of this trigger circuit 22 is supplied to a conventional one-shot multivibrator 24.

This one-shot multivibrator 24 is connected to the sample and hold circuit 20 for the purpose of controlling the operation of the sample and hold circuit 20. It will be realized that the trigger circuit 22 and the one-shot 24 are employed in order to "time" or reset the operation of the sample and hold circuit 20 in such a manner as to obtain a signal as indicated in the curve adjacent to the circuit 20 varying in amplitude at time intervals corresponding to peaks of a pulse as represented by the signal which is the output of the amplifier 16 and which is of a constant value between these individual peaks.

This output signal from the sample and hold circuit 20 is passed through a conventional protective diode 26 to a conventional type of differentiator 28 which is utilized to provide a signal as indicated by the curve adjacent to this differentiator 28 having peaks or spikes which are spaced from one another an amount corresponding to the time intervals between the peaks of the pulses and which vary in magnitude with the differences in magnitude between successive pulse peaks.

This output from the differentiator 28 may, and preferably is, sent through a conventional filter circuit 30 to a variable frequency oscillator 32 which is intended to supply an output signal having a shape corresponding to the curve by this oscillator 32 to another amplifier 34. This filter circuit 30 may be referred to as an enveloping circuit because its function is to reform the shape of the signal from the differentiator 28 to a shape as shown.

The output of this amplifier 34 is fed through a conventional volume control 36 to a speaker 38 which will provide a variable frequency tone corresponding to the shape of the signal from the filter circuit 30 which may be audibly sensed by an individual. The nature of the tone obtained is considered desirable in avoiding what may be referred to as a "hypnotic effect" since it not only varies in frequency so as to correspond to intrathoracic pressure and heart action but in addition varies in frequency between successive pulse peaks. Thus, it is not an essentially continuous tone or a "monotone".

This tone will indicate the manner in which the heart of the individual is operating and thus will provide an indirect indication of the intrathoracic pressure in accordance with the variation of the heart operation. By appropriate instruction an individual will be able to learn or can be taught to learn that a specific tone is desirable as indicating a desired comparatively low intrathoracic pressure and can gradually learn to control his or her heart so as to cause the heart to operate in such a manner that there is little, if any, danger of heart failure resulting from the heart operating so as to increase the flow of blood to the lungs.

Although it is possible to utilize an output or output signal obtained by signal monitoring and signal modification means as described corresponding to variations in the amplitude of the pulse to operate lights, vibrators or the like capable of being sensed by the body, it is preferred to utilize a signal modified as described to provide a variable frequency tone since the human ear is normally reasonably sensitive to tonal changes. Further the use of a tone as described permits an individual to close his or her eyes while listening to the tone.

This minimizes the possibility of distractions tending to interfere with the individual's concentrating on the feedback signal and in obtaining a desired heart action while breathing. However, with certain individuals it may be advisable to provide a visual indication such as a volt meter to provide a feedback output as, for example, when the individual has hearing problems. A switch can be employed to select which of several outputs is most desirable for use as a feedback signal with a particular patient.

I claim:

1. A process for treating an individual having an obstructive lung disorder so that such an individual controls the manner in which his or her heart operates so as to control the individual's intrathoracic pressure which comprises the steps of:

monitoring the pulse of the individual so as to obtain a signal varying in accordance with the peak values of each pulse beat, and using said signal to provide to the individual an output which is capable of being sensed by the individual and which corresponds to this signal; and varying the heart activity of the individual by the individual in accordance with said output so as to have the individual's heart action and breathing achieve a desired intrathoracic pressure.

2. A process as claimed in claim 1 wherein: said output is a variable frequency tone.

3. A process as claimed in claim 1 wherein:

the pulse of the individual is monitored so as to obtain a signal corresponding to the variation of the peak values of each pulse beat of the individual, and said signal corresponding to each pulse beat of the individual is modified in order to provide a further signal corresponding to the differences in the amplitudes of successive monitored pulse beats, and said further signal is used to provide a variable frequency tone serving as said output, the frequency of said tone corresponding to the differences in the amplitudes of successive monitored pulse beats.

* * * * *